United States Patent [19]
Swanson

[11] Patent Number: 5,947,132
[45] Date of Patent: Sep. 7, 1999

[54] FLOSSING LOOPS AND ASSOCIATED PACKAGING ARRANGEMENTS

[76] Inventor: Glen Swanson, 1418 Darwin Dr., Oceanside, Calif. 92056

[21] Appl. No.: 09/175,524

[22] Filed: Oct. 20, 1998

[51] Int. Cl.[6] .................................................. A61C 15/00
[52] U.S. Cl. ......................... 132/321; 132/323; 132/324; 132/325; 132/326
[58] Field of Search .................................. 132/321, 322, 132/323, 324, 325, 326, 327, 328; 206/63.5, 820

[56] References Cited

U.S. PATENT DOCUMENTS

| | | | |
|---|---|---|---|
| 309,959 | 8/1884 | Endelson | D28/64 |
| 4,034,770 | 7/1977 | Trecker | 132/90 |
| 4,315,517 | 2/1982 | Krag | 132/321 |
| 4,330,014 | 5/1982 | Glass et al. | 132/321 |
| 4,364,380 | 12/1982 | Lewis | 132/321 |
| 4,523,600 | 6/1985 | Donovan | 132/321 |
| 4,706,843 | 11/1987 | Thornton | 221/48 |
| 4,986,289 | 1/1991 | McWhorter | 132/323 |
| 5,014,725 | 5/1991 | Patscot | 132/324 |
| 5,086,792 | 2/1992 | Chodorow | 132/323 |
| 5,222,510 | 6/1993 | Zuehlsdorf | 132/323 |
| 5,435,330 | 7/1995 | Dix | 132/323 |
| 5,454,386 | 10/1995 | Dix | 132/323 |
| 5,650,035 | 7/1997 | McGaha et al. | 156/443 |
| 5,682,912 | 11/1997 | Desiderio | 132/321 |
| 5,799,673 | 1/1997 | Amendola et al. | 132/321 |

*Primary Examiner*—John J. Wilson
*Assistant Examiner*—Trang Doan
*Attorney, Agent, or Firm*—Goldstein & Canino

[57] ABSTRACT

A flossing loop comprising a closed or continuous loop of dental floss standing, or alternately formed by a length of dental floss having a first and second end, with the first end of the length of dental floss secured to the second end to form the closed loop. A plurality of the flossing loops may be arranged as a cascade of frangibly coupled flossing loops that are contained in a suitable package. The package is configured with a suitable opening, possibly provided as a slot, to enable each respective flossing loop (of the cascade) to be drawn out of the package, one after the other. Once a respective flossing loop is drawn from the package it is detached from the next subsequent flossing loop still substantially located within the chamber, and is available for flossing activities.

3 Claims, 4 Drawing Sheets

FLOSSING LOOPS AND ASSOCIATED PACKAGING ARRANGEMENTS

BACKGROUND OF THE INVENTION

1. Field of the Invention

The present invention relates to dental flossing devices. More particularly, the invention relates to a flossing loop formed as a continuous loop of a strand of dental floss, or alternately, as a length of dental floss that is secured in a loop by a suitable securing means.

2. Background and Objects of the Invention

The need for proper and regular cleaning of ones teeth has been well established. A range of devices have been devised to enable an individual to effect dental cleaning. These devices range from the ubiquitous tooth brush to sophisticated battery and AC powered devices such as irrigators and power flossers. One very simple, low cost, and commonly recommended cleaning item, which is particularly suited for cleaning between ones teeth is dental floss.

Dental floss is constructed as a thin string (or strand) typically formed of a large plurality of woven stringy fibers. Often floss is purchased and packaged in a container having an internal chamber for securely holding a large continuous length of floss wrapped around a spool or bobbin. The container is arranged to enable a length of floss to be drawn and separated from the spooled portion remaining within the container. A most common method of using the length of separated floss is to simply wrap or coil one end around a finger on each hand (of a user). The user than places a center portion of the length of floss in his or her mouth, and often with the aid of one or more additional fingers carries out flossing activities. One disadvantage of using dental floss in this manner is that eventually the user's fingers experience discomfort due to the tightening of the floss around the wrapped fingers during flossing. This may lead some individuals to shorten the time spent flossing. Also, it is common for the floss to slip and loosen from around a users fingers. The latter problem may be remedied by applying several additional coils of floss around each finger to better secure the floss during use. However, this only exacerbates the discomfort experienced from floss tightening around the fingers of the user.

A number of prior art devices have been proposed to enable flossing with either standard dental floss employed with a device that secures the floss for in-mouth use, or alternately, employs one of more lengths of floss in combination with 'holding aids', wherein the length(s) can be easily grasped without having to wrap floss around ones fingers. One example, provided by U.S. Pat. No. 5,435,330 to Dix suggests the use of 'ring portions' that are fixed to each end of a length of floss. The ring portions are arranged to enable a user to slip his/her finger thorough each ring during flossing. Although this invention does lessen the finger discomfort experienced by a user, it results in a flossing device that is difficult to package in a small and easy to carry package. Also, the diameter of the ring portions may, most ideally, need to be varied with the size of a users fingers. U.S. Pat. No. 4,034,770 to Trecker discloses a device not unlike the Dix invention, in that holding or grasping aids are included.

Another prior art device disclosed by U.S. Pat. No. 5,086,792 to Chodorow provides for a pair of parallel floss strands having their ends secured to a pair of spaced apart gripping elements. The combination of the strands and the gripping elements result in a loop being formed. However, it is believed that the arrangement provided by Chodorow will be difficult to use and manipulate during flossing activities due to the presence of two equal length strands. Further, as with the Dix invention, packaging, especially in a small package with a large number of flossing devices therein, is difficult if not impossible.

Therefore, when considering prior art flossing devices and arrangements, there is a need for a very simple, easy to use flossing device configured to overcome the above stated problems. Accordingly, objects of the present invention are to provide new and improved dental flossing devices having one or more of the following capabilities, features, characteristics, or advantages:

provides a simple flossing loop arrangement;

easy to use without causing pain and discomfort to fingers of a user;

may be packaged with at least a relatively large number of flossing loops housed in a suitable packaging arrangement;

may include a holding or securing 'bead' to enable a (linear) length of floss stranding to be formed and configured in a loop in accordance with the invention;

may include a means to enable a cascade of flossing loops to be drawn from a packaging arrangement, one at a time (as needed), wherein each flossing loop drawn from the packaging arrangement is easily separated from the cascade; and including low cost, easy to manufacture embodiments.

The above listed objects, advantages, and associated novel features of the contemplated embodiments of the present invention, as well as others, will become more apparent with a careful review of the description and figures provided within this disclosure. Attention is called to the fact, however, that the drawings and the associated description are illustrative and exemplary only, and variations are certainly possible.

SUMMARY OF THE INVENTION

In accordance with the present invention, a dental floss dispensing arrangement is provided that includes a plurality of individual flossing loops. Each flossing loop is formed of a length of a dental floss strand, which is arranged in a closed loop. A means is provided to frangibly attach each respective flossing loop to a next respective flossing loop forming what may be termed 'a cascade of flossing loops'. The cascade of flossing loops are contained a packaging arrangement having a wall structure to establish an internal chamber suitable to hold a plurality of the flossing loops. The packaging arrangement includes an opening, possibly realized as a slot, to enable each respective flossing loop (of the cascade) to be drawn out of the internal chamber, one after the other. Once a respective flossing loop is drawn from the internal chamber it may be easily detached from the next subsequent flossing loop, which is substantially still located within the internal chamber. The detaching of one flossing loop from another is made possible by a frangible attaching means that couples one flossing loop to the next in the cascade.

In a preferred embodiment of the present invention, each flossing loop is formed by a length of a dental floss strand, which is arranged in a closed loop. This embodiment provides for a continuous closed loop arrangement of a flossing strand. Alternately, the flossing loops may be formed by a length of a dental floss strand having a first end and a second end, wherein a means is employed to secure the first end of the length of dental floss to the second end to form a loop suitable for use in flossing the teeth of a user. As skilled persons will appreciate, the means for securing the first and second ends may be provided in a number of suitable arrangements. For example, said means may be provided by a molded plastic bead configured to securely fasten the first and second ends.

BRIEF DESCRIPTION OF THE DRAWINGS

In the drawings, like elements are assigned like reference numerals. The drawings are not necessarily to scale, with the emphasis instead placed upon the principles of the present invention. Additionally, each of the embodiments depicted are but one of a number of possible arrangements utilizing the fundamental concepts of the present invention. The drawings are briefly described as follows:

FIG. 2C illustrated a modified securing bead that supports the cascading of a plurality of flossing loops.

LIST OF REFERENCE NUMERALS USED IN THE DRAWINGS

10—flossing loop
10a—flossing loop (alternate embodiment)
12—length of (dental) floss strand or string
12a—first end of (dental) floss strand or string
12b—second end of (dental) floss strand or string
14—bead
14a—bead with angled slot
14aa—angled slot of bead 14a
16—cascade of flossing loops
18—loop of thread
22—packaging arrangement
22a—wall structure (of the packaging arrangement)
24—(first) flexible elongated strip
24a—first side of first flexible elongated strip
25—second flexible elongated strip
26—opening (round)
26a—opening (slot)
28—pouch or pocket (for holding flossing loop)

DETAILED DESCRIPTION OF THE PREFERRED EMBODIMENTS

It is important to establish the definition of several terms and expressions that will be used throughout this disclosure. The term 'packaging arrangement' is to be defined broadly, and may include any suitable container, including those illustrated in FIGS. 3 and 4, that may contain a plurality of flossing loops, and enable said flossing loops to be dispensed. The expressions 'flossing' or 'flossing activities', which are well known in the art, are to include the placing of a portion of the length of dental floss stand comprising the flossing loops into a space or crack between two adjacent teeth and moving the flossing loop appropriately to commence and conduct cleaning of the teeth and the area therebetween. Additional terms and expressions will be defined below, as required.

Figure 1A:
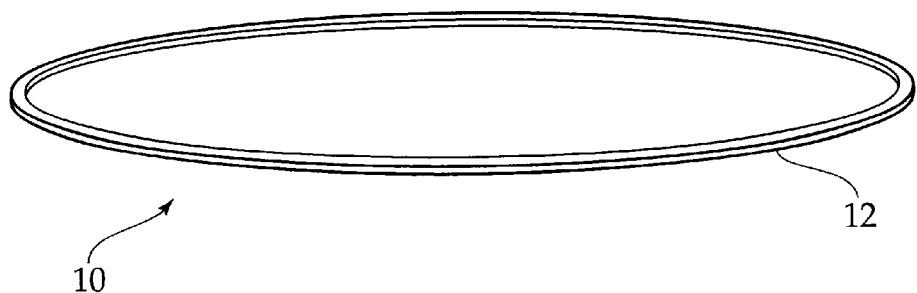
FIGS. 1A and 1B provide embodiments of the flossing loops in accordance with the present invention.
Figure 1B:
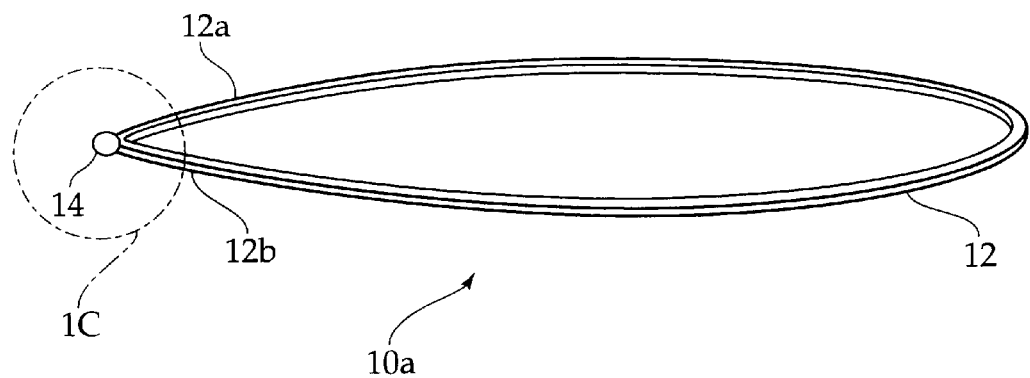

Turning now to FIG. 1A, there is depicted a flossing loop 10 formed of a length of a dental floss strand 12, which is arranged in a closed or continuous loop. The closed loop construction of the flossing loop 10, whether constructed as shown in FIG. 1A, or alternately, as shown in FIG. 1B, is intended to enable a user to floss his or her teeth without having to wrap the floss strand 12 around one or more fingers one or more times. The flossing loop 10 is contemplated to be providable in one of a plurality of predetermined diameters, which may be selected based on the size of a user's hand. For example, a young person having relatively small hands may require the flossing loop to have a diameter of, for example, 10 centimeters, while an adult may require a diameter of 12 to 15 centimeters.

Figure 1C:
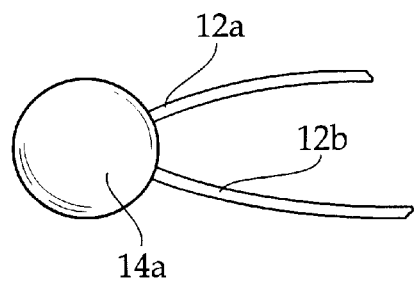
FIG. 1C provides an enlarged view of a securing bead as shown in FIG. 1B.

Another embodiment of the flossing loop 10, which may also be termed a flossing device, is shown in FIG. 1B. Flossing loop 10a is comprised of a length of a dental floss strand 12 having a first end 12a and a second end 12b. The first end 12a and second end 12b are clearly seen in FIG. 1C. Also shown in FIGS. 1B and 1C, is a means to secure the first end 12a of the length of dental floss 12 to the second end 12b to form a loop suitable for use in flossing ones teeth. As those skilled in the art would appreciate, a number of means are available to secure the first and second ends of the length of floss 12. One preferable means to secure the first end 12a of the length of floss strand 12 to the second end 12b is provided by a molded plastic bead 14 configured to securely fasten the first end 12a to the second end 12b. In a possibly most preferred embodiment of the flossing loop 10a, a seen in FIGS. 2B and 2C, the plastic molded bead may be modified and formed having an angled slot 14aa provided therein. The modified bead 14a is configured with the angled slot 14aa to enable a plurality of the flossing loops 10a to be cascaded, as can be seen in FIG. 2B. The arrangement of FIG. 2B may be termed 'a cascade of flossing devices or flossing loops', which may be drawn from a suitable packaging arrangement, such as that shown in FIGS. 3 and 4, one after the other, and frangibly detached (from each other).

Figure 2A:
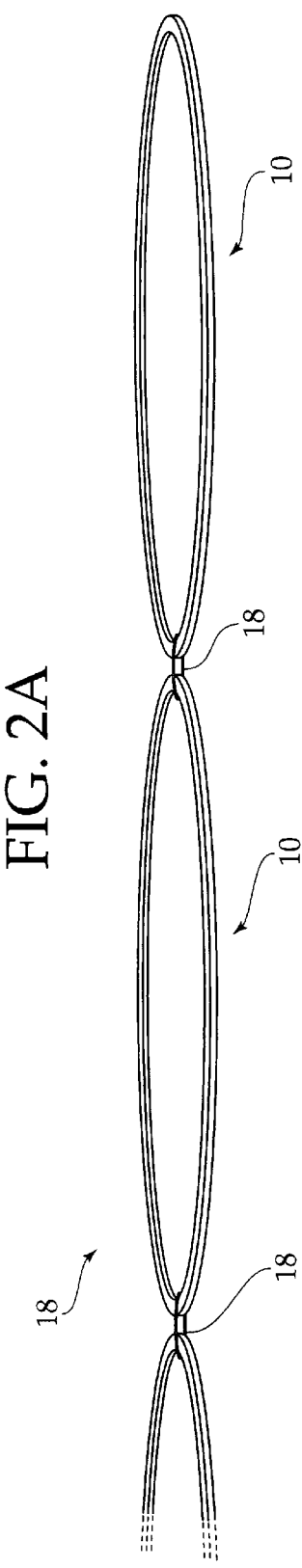
FIGS. 2A and 2B depict cascades formed by frangibly coupled flossing loops.
Figure 2B:
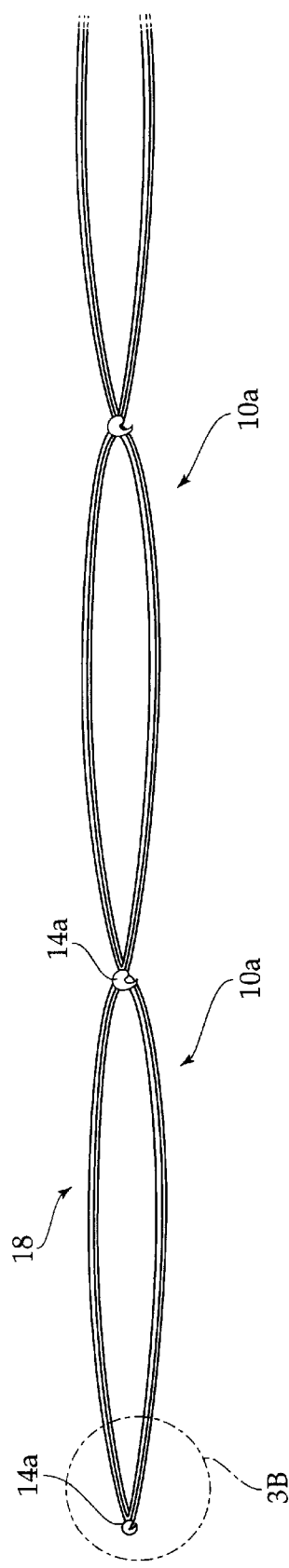

The flossing loop 10 of FIG. 1A may be cascaded as illustrated in FIG. 2A. As shown therein, a plurality of individual flossing loops 10, with each flossing loop formed of a length of a dental floss strand is arranged in a closed loop are cascaded. A means to frangibly attach one flossing loop 10 to a next flossing loop may be provided by a fine coupling loop comprised of, for example, a light easy to rupture loop of thread 18 that wraps around two consecutive flossing loops in the cascade of flossing loops 10. Skilled persons may provide other coupling arrangements that may be employed with the present invention to form cascades of flossing loops 10.

Figure 3B:
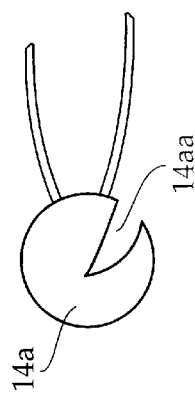
FIG. 3 shows an embodiment of a packaging arrangement configured to hold and dispense a cascade of flossing loops.
Figure 3:
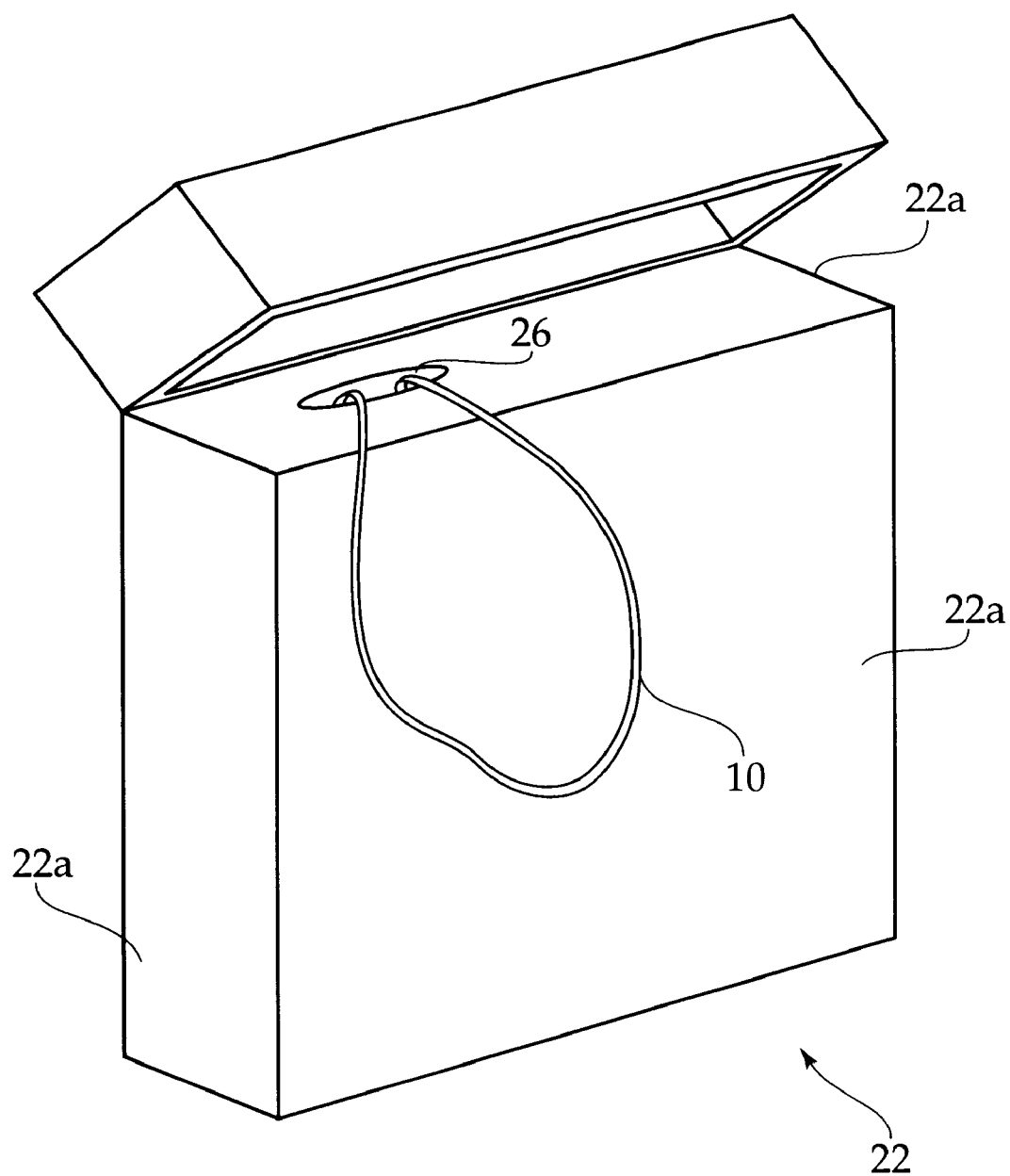

Referring now to FIG. 3, a packaging arrangement 22 having a wall structure 22a comprised of a plurality of side portions may be provided. The wall structure 22a establishes an internal chamber suitable to hold the plurality of flossing loops, most preferably arranged in a cascade (as discussed above). The packaging arrangement 22 would preferably include an opening 26 in the wall structure 22a to enable each respective flossing loop 10/10a of the cascade to be drawn out, one after the other, so that a respective flossing loop drawn from the internal chamber may be detached from the next subsequent flossing loop to which it is frangibly attached. This would preferably leave the next flossing loop 10/10a of the cascade in position, substantially still contained within the packaging arrangement 22, for easy removal when another flossing loop 10/10a is later needed.

Figure 4:
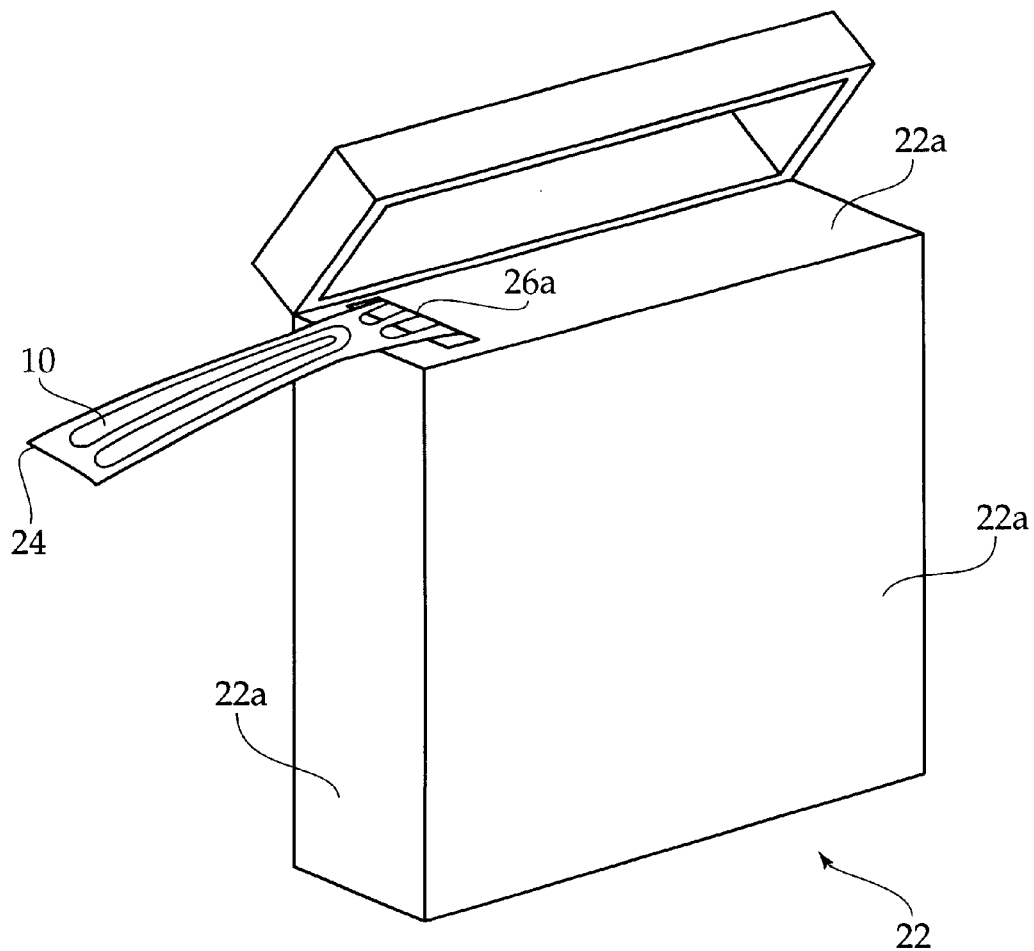
FIG. 4 provides an embodiment of another arrangement for holding and dispensing the flossing loops of the present invention.
Figure 5:
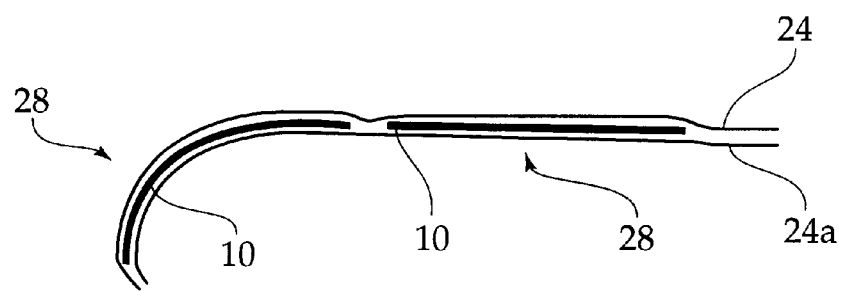
FIG. 5 depicts yet another arrangement for holding and dispensing flossing loops.

A number of other possible packaging arrangements are possible. For example, when considering flossing loops 10 of FIG. 1A, a flexible elongated strip 24, as shown in FIG. 4, may be provided (that is coiled) having a plurality of the flossing loops 10 removably fixed to a first side 24a thereof at spaced locations along the elongated strip 24. As can be seen in FIG. 4, a packaging arrangement 22 having a wall structure 22a may be provided to establish an internal chamber suitable to securely hold the elongated strip, while coiled. The packaging arrangement 22 is further contemplated to include a slotted opening 24a, or another suitable opening arrangement, to enable a portion of the elongated strip 24 to be drawn out of the internal chamber. The drawing out of the portion of the elongated strip 24 would result in a length (of the elongated strip) being uncoiled to enable one of the plurality of flossing loops 10 to be accessed and removed for subsequent use in flossing activities. It should be noted that a second elongated strip 25, which is superposed over the first strip 24, so as to sandwich each of the flossing loops 10 therebetween, may be provided as shown in FIG. 5. This arrangement of may enable pockets or pouches 28 to be formed to hold each of the plurality of flossing loops contained in the packaging arrangement 22, and further enable their easy dispensing.

It is important to understand that the description of the embodiments of the flossing loops and the packaging arrangements provided to contain and dispense said flossing loops are illustrative only, and other equivalent arrangements are certainly possible. For example, the function of the bead 14 may be provided in many ways including a simple knotting of the flossing strand 12. Therefore, while there have been described the currently preferred embodiments of the invention, those skilled in the art will recognize that other and further modifications may be made without departing from the present invention, and it is intended to claim all such modifications and variations as fall within the scope of the appended claims.

What is claimed is:

1. A dental floss dispensing arrangement, comprising:

a) a plurality of individual flossing loops, each flossing loop formed of a length of a dental floss strand, which is arranged in a closed loop;

b) means to frangibly attach each respective flossing loop to a next respective flossing loop is provided by a fine coupling loop comprised of a light easy to rupture loop of thread that wraps around two consecutive flossing loops and forms a cascade of flossing loops; and c) a packaging arrangement having a wall structure to establish an internal chamber suitable to hold the plurality of flossing loops;

d) the packaging arrangement including an opening to enable each respective flossing loop of the cascade to be drawn out of the internal chamber, one after the other, so that a respective flossing loop drawn from the internal chamber may be detached from a next subsequent flossing loop to which it is frangibly attached and which is substantially still contained within the packaging arrangement.

2. A dental flossing device, comprising:

a) a length of a dental floss strand having a first end and a second end; and b) a bead configured to securely fasten the first end of the length of dental floss to the second end to form a loop suitable for use in flossing a user's teeth;

c) a molded plastic bead, having an angled slot formed therein, the angled slot enabling a plurality of the flossing devices to be removeably attached to form a cascade of flossing devices, one following the other.

3. The dental flossing device in accordance with claim 2, further including a packaging arrangement having a wall structure to establish an internal chamber suitable to hold the cascade of dental flossing devices, with the packaging arrangement including an opening to enable each respective flossing device of the cascade to be drawn out of the internal chamber, one after the other, so that a respective flossing device drawn from the internal chamber may be detached from the next subsequent flossing device.

* * * * *